United States Patent [19] [11] 4,056,564
Wolf et al. [45] Nov. 1, 1977

[54] DIHYDROXY SULPHONATES CONTAINING ETHER STRUCTURES

[75] Inventors: Gerhard Dieter Wolf, Dormagen; Francis Bentz, Cologne; Günther Nischk, Dormagen, all of Germany

[73] Assignee: Bayer Aktiengesellschaft, Leverkusen, Germany

[21] Appl. No.: 598,104

[22] Filed: July 22, 1975

[30] Foreign Application Priority Data

Aug. 2, 1974 Germany .............................. 2437218

[51] Int. Cl.$^2$ .................. C07C 143/42; C07C 143/11; C08G 63/12; C08C 69/44

[52] U.S. Cl. ............................ 260/512 C; 260/513 R; 260/513 B; 260/75 S; 260/78 R; 260/77.5 R; 526/3

[58] Field of Search ............ 260/513 R, 513 B, 512 C

[56] References Cited

U.S. PATENT DOCUMENTS

| | | | |
|---|---|---|---|
| 3,102,893 | 9/1963 | Gaertner | 260/513 B |
| 3,860,638 | 1/1975 | Beach et al. | 260/513 B |
| 3,879,450 | 4/1975 | Velker et al. | 260/513 B |

*Primary Examiner*—Bernard Helfin
*Assistant Examiner*—Nicky Chan
*Attorney, Agent, or Firm*—Gene Harsh; Joseph C. Gil; William E. Parry

[57] ABSTRACT

The instant invention relates to dihydroxy sulphonates containing ether groups, and to a process for their production. They are obtained by the addition of bisulphites to (poly)alkoxylated dihydroxy alkenes.

2 Claims, No Drawings

DIHYDROXY SULPHONATES CONTAINING ETHER STRUCTURES

BACKGROUND OF THE INVENTION

It is known that alkali metal bisulphites may be added to double bonds activated by electron-attracting groups such as nitrile or ester groups [cf. R. T. E. Schenck and J. Danishefsky, J. Org. Chem. 16, 1683 (1951); O. Bayer, Ang. Chem. 61, 233 (1949)]. It is also known that bisulphites may be added to aliphatic double bonds which are only weakly activated. Thus, the addition of bisulphites to allyl alcohol is described in the literature [cf. M. S. Kharasch, E. M. May and F. R. Moyo, J. Org. Chem. 3, 1975 (1939)]. This reaction produced 3-hydroxy propane sulphonic acid in the form of its salts in a yield of only 30%. Although the yield of this reaction was increased (see, e.g. German Pat. No. 915,693), it was not possible to suppress the formation of secondary products which are assumed to be compounds of the following structure:

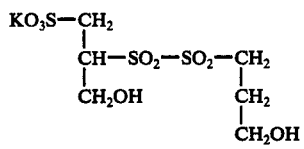

Additionally, complete separation of the inorganic salts formed during the reaction from the sulphonate is difficult.

Salts of 3-hydroxy-2-hydroxy methyl propane sulphonic acid are also known and can be obtained by reacting 2-methylene-1,3-propane diol with bisulphites (see, e.g. German Offenlegungsschrift No. 2,224,304). However, 2-methylene-1,3-propane diol can only be obtained in small quantities at considerable expense, so that the salts of 3-hydroxy-2-hydroxy methyl-1-propane sulphonic acid obtained therefrom cannot be used on a wide scale. In addition, it is relatively difficult to separate the salts of 3-hydroxy-2-hydroxy methyl propane sulphonic acid from the inorganic salts formed during the reaction. This also applies to the production of salts of 1,4-dihydroxy-2-butane sulphonic acid which may be used for the preparation of stable baths for copper plating in the absence of an electrical current (see, e.g. German Offenlegungsschrift No. 2,132,003).

Accordingly, there is a need for dihydroxy sulphonate which may be produced easily and inexpensively and which, in addition, may be used for a variety of applications by virtue of their favorable properties.

DESCRIPTION OF THE INVENTION

It has now surprisingly been found that bisulphites can be added to alkoxylated dihydroxy alkenes in high yields and purity.

Accordingly, the present invention relates to dihydroxy sulphonates containing ether groups and corresponding to the following general formula:

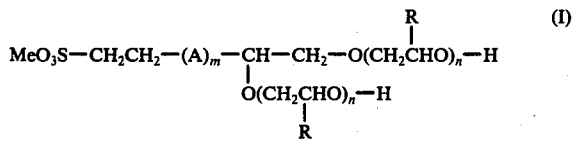

wherein

A represents a straight- or branched-chain alkylene radical having from 1 to 6 carbon atoms;

R represents hydrogen, a $C_1$-$C_4$ alkyl radical or phenyl;

Me represents $NH_4$ or an alkali metal;

n is a number of from 1 to 30, preferably from 1 to 10; and m is 1 or, preferably, 0.

The invention also relates to a process for the production of these compounds which is distinguished by the fact that unsaturated diols corresponding to the following general formula:

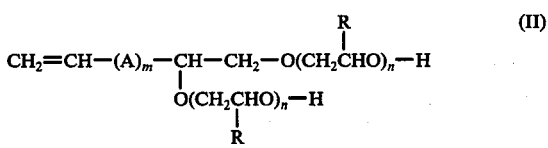

wherein

A, R, Me, n and m are as defined above;
are reacted with bisulphites corresponding to the following general formula:

$$MeHSO_3$$

wherein

Me represents $NH_4$ or an alkali metal,
in aqueous medium, in the presence of catalytically active oxygen, at temperatures of up to 100° C and at pH-values in the range of from 3 to 9, and preferably in the range from 7 to 8, the molar ratio of bisulphite to diol being from 1:1 to 5:1.

These dihydroxy sulphonates containing ether groups can be obtained in highly pure form and in very good yields by the method described above. Separation of the inorganic salts formed during the reaction is surprisingly easy and is carried out by extracting the sulphonates with acetone, acetone/water mixtures, chlorinated hydrocarbons, alcohols or alcohol/water mixtures. After extraction, the sulphonates do not contain any salts (even minute quantities cannot be detected).

In addition to this easy and quantitative separation of the inorganic salts, another advantage which should be mentioned is the wise scope of application of the compounds according to the invention. They are eminently suitable for use as comonomers for the production of acid-modified polyesters and polyurethanes and, after they have been reacted for example with chloroacetic acid (esters), are useful for the production of acid-modified polyamides. The derivatives which are more highly ethoxylated and/or propoxylated, optionally after reaction with isocyanates, for example to form diurethanes, are excellent antistatic agents and are used as additives in the production of antistatically-finished films, sheets and filaments of polyacrylonitrile or polyamide.

The unsaturated diols used as starting products may be obtained in known manner by (poly)alkoxylating dihydroxy alkenes corresponding to the following general formula:

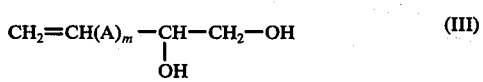

wherein

A represents a straight- or branched-chain alkylene radical having from 1 to 6 carbon atoms; and m is 1 or, preferably, 0. The alkoxylating agents used are known and include such mterials as ethylene oxide, propylene oxide, butylene oxide or styrene oxide. This alkoxylation reaction is carried out in the absence or presence of solvents, such as dioxane or DMF, and in the presence of small quantities preferably from 0.2 to 2% by weight of a basic catalyst, such as NaOH, KOH, sodium or potassium methylate, at temperatures in the range of from 50° to 180° C, preferably at temperatures in the range of from 100° to 160° C, and optionally under pressure in an autoclave. Substances ranging from highly viscous to wax-like are formed and may be characterized by their degree of alkoxylation by determining the OH-number or by NMR-spectroscopy.

Sulphonation may be carried out using commercial-grade bisulphite liquors or with bisulphite liquors freshly prepared by introducing SO$_2$ into the corresponding aqueous ammonium or alkali metal hydroxide solution. The bisulphites usable are known in the art.

The addition reaction may be carried out at temperatures of up to 100° C, preferably from −10° C to 70° C and most preferably at room temperature, by introducing the unsaturated diols or their aqueous solutions into, or slowly adding them dropwise, to the bisulphite liquor. The molar ratio of bisulphite to diol should be in the range of from 1:1 to 5:1, and is preferably in the range of from 1.1:1 to 2:1. Catalyst suitable for the reaction include air, oxygen or oxygen-yielding compounds such as H$_2$O$_2$, the oxygen having to be present in the reaction mixture in as fine a state of dispersion as possible, which may readily be achieved by means of suitable stirrers. A high yield of sulphonate is dependent upon the pH-value of the reaction solution which should be in the range of from 3 to 9, pH-values in the range of from 5 to 8 being preferred, and a pH-value of about 7 being particularly preferred. The required pH-value is adjusted by adding the necessary quantity of ammonia or alkali liquor, for example, to the bisulphite solution. During the reaction, the pH-value increases. However, the pH-value is maintained at the required value by simultaneously adding dilute acid or by introducing more sulphur dioxide. The reaction is complete when there is no further change in the pH-value. Heat is given off during the reaction and if desired, may be cooled.

In cases where unsaturated diols with a relatively high degree of alkoxylation are reacted, it is advisable initially to introduce the unsaturated diol into the reactor, followed by dropwise addition of the solution of the bisulphite, but again under the reaction conditions described above.

Separation of most of the inorganic salts is preferably carried out by concentrating the solution to approximately half its volume and filtering off the crystals precipitated. The required reaction products may be separated off from the residual inorganic salts by extraction with acetone, acetone/water mixtures, chlorinated hydrocarbons, alcohols and alcohol/water mixtures. The sulphonates accumulate in analytically pure form in yields of up to 90%.

The sulphonates containing ether groups produced in accordance with the invention are eminently suitable for use as comonomers for the production of acid-modified polyesters and polyurethanes and, after they have been reacted, for example, with chloroacetic acid (esters), also for the production of acid-modified polyamides. In addition, the derivatives which are more highly ethoxylated and/or propoxylated optionally after reaction with isocyanates to form diurethanes, are excellent anistatic agents and are used as additives in the production of polyacrylonitrile or polyamide sheets, films and filaments with antistatic properties.

The production of a copolyester for polyester fibers dyeable with basic dye is described in the following:

194.0 parts by weight of terephthalic acid dimethyl ester, 186.0 parts by weight of ethylene glycol and 12.4 parts by weight of a dihydroxy sulphonate corresponding to the following formula:

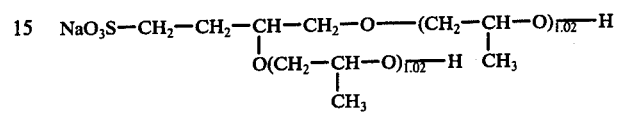

in admixture with 0.5 parts by weight of zinc acetate and 0.6 parts by weight of antimony trioxide, are introduced into a reaction vessel equipped with an anchor agitator, gas inlet pipe, dephlegmator, condenser, vacuum adaptor and receiver. The contents of the reaction vessel are heated to approximately 165° C while nitrogen is passed thereover, followed by transesterification for 2 hours. The temperature is then increased to 280° C over a period of 3 hours. After the supply of nitrogen has been shut off, the pressure is gradually reduced over a period of 1 hour to 0.03 Torr. The speed of the stirrer then has to be reduced from approximately 150 to approximately 20 revolutions per minute because of the steady increase in the viscosity of the melt. Polycondensation is complete after another 4 hours. The colorless, homogeneous highly viscous melt may be processed into shaped articles, especially filaments. The stretched filaments may be dyed dark blue with a basic dye. The dye finish is washproof.

The polyester has a softening point of from 254 to 264° C and a relative solution viscosity $\eta_{rel.}$ of 2.02 (as measured on a solution of 1 g of substance in 100 ml of m-cresol at a temperature of 25° C).

The invention is further illustrated, but is not intended to be limited by the following examples in which all parts and percentages are by weight unless otherwise specified.

EXAMPLE 1

Ethoxylated 1,2-dihydroxy-3-butene

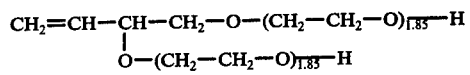

2.6 g of sodium were added to 264 g (3 mols) of 1,2-dihydroxy-3-butene, and the resulting mixture reacted in an autoclave at from 100° to 110° C with 528 g (12 mols) of ethylene oxide, the ethylene oxide being added during the reaction. The ethylene oxide was added in such a way that an internal pressure of at most 3 to 4 atms was maintained throughout the reaction. The reaction mixture was then stirred until the excess pressure had disappeared. Determination of the content of OH-groups produced a figure of 13.56 OH%, corresponding to a molecular weight of 250.8 and to a total ethylene oxide content 2 $n$ = 3.7.

EXAMPLE 2

Propoxylated 1,2-dihydroxy-3-butene

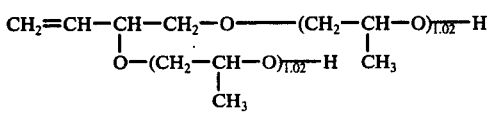

As in Example 1, 1% of sodium was added as catalyst to 264 g (3 mols) of 1,2-dihydroxy-3-butene and the resulting mixture reacted in an autoclave at from 140° to 150° C with 348 g (6 mols) of propylene oxide. Determination of the content of OH-groups produced a figure of 16.52 OH%, corresponding to a molecular weight of 206 and to a total propylene oxide content of $2n = 2.04$.

EXAMPLE 3

Ethoxylated butane diol sulphonate

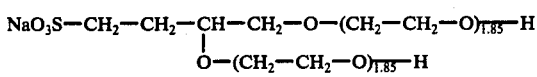

250.8 g (1 mol) of ethoxylated 1,2-dihydroxy-3-butene (prepared in accordance with Example 1) were dissolved in 750 ml of water, followed by the dropwise addition of 260 g (1 mol) of a 40% sodium bisulphite solution adjusted to pH 7.1 with dilute sodium hydroxide. The reaction was started by blowing in air through a glass frit, producing an increase in temperature and pH-value.

The pH-value was maintained at from 7.0 to 7.1 by the dropwise addition of dilute sulphuric acid. The reaction was complete when the pH-value remained constant or when the pH of the reaction mixture assumed an acid value through the dropwise addition of the sulphuric acid. The aqueous neutral solution was concentrated by drying and the sulphonate extracted with methanol. Yield: 298 g (84% of the theoretical yield).

EXAMPLE 4

Propoxylated butane diol sulphonate

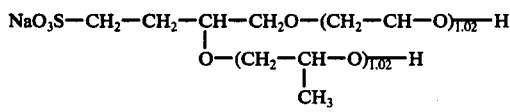

As in Example 3, 206 g (1 mol) of propoxylated 1,2-dihydroxy-3-butene (prepared in accordance with Example 2) were introduced into 600 ml of water. 260 g (1 mol) of 40% sodium bisulphite solution ws then added dropwise in the presence of finely-dispersed air. The pH-value of the reaction medium was maintained at from 7 to 7.1 by the dropwise addition of dilutesulphuric acid. The aqueous solution was then concentrated by drying and the sulphonate extracted with methylene chloride. Yield: 260 g (84% of the theoretical yield)

EXAMPLE 5

Propoxylated butane diol sulphonate

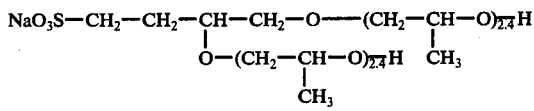

366.4 (1 mol) of propoxylated 1,2-dihydroxy-3-butene with a total degree of propoxylation of $2n = 4.8$ were dissolved in 1000 ml of water, followed by the dropwise addition of 260 g of a 40% sodium bisulphite solution at pH 7-7.1 in the presence of finely-dispersed air. On completion of the addition, the sulphonate was extracted with methylene chloride. Yield: 419 g (89% of the theoretical yield).

EXAMPLE 6

Propoxylated butane diol sulphonate

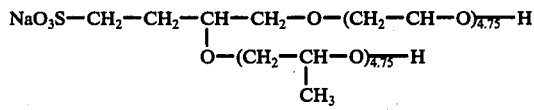

A 40% sodium bisulphite solution was added as in Example 5 to 640 g of propoxylated 1,2-dihydroxy-3-butene (total degree of propxylation $2n = 9.5$) in aqueous solution in the presence of finely-dispersed air at a pH-value maintained at 7.0-7.1 After the neutral aqueous solution had been concentrated by drying, the product was extracted with methylene chloride. It was obtained in a yield of 86% (640 g).

What is claimed is:

1. Dihydroxy sulphonates containing ether groups and corresponding to the following general formula:

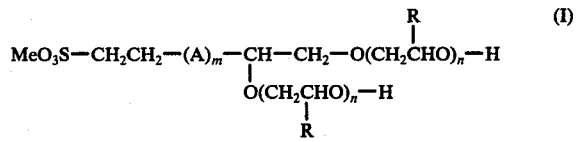

wherein

A represents a straight- or branched-chain alkylene radical having from 1 to 6 carbon atoms;

R represents hydrogen, a $C_1-C_4$ alkyl radical or phenyl;

Me represents $NH_4$ or an alkali metal;

m is 0 or 1; and n is a number of from 1 to 30.

2. Dihydroxy sulphonates containing ether groups as claimed in claim 1, wherein m in general formula (I) is 0.

* * * * *